United States Patent [19]

Heller

[11] 4,108,604

[45] Aug. 22, 1978

[54] ANALYTICAL METHOD FOR TNT IN WATER

[75] Inventor: Carl A. Heller, China Lake, Calif.

[73] Assignee: The United States of America as represented by the Secretary of the Navy, Washington, D.C.

[21] Appl. No.: 816,225

[22] Filed: Jul. 18, 1977

[51] Int. Cl.$^2$ .................... G01N 21/06; G01N 33/18; G01N 33/22

[52] U.S. Cl. .............................. 23/230 R; 23/230 M; 23/253 TP

[58] Field of Search ........ 23/2 30 R, 230 M, 253 TP, 23/232 R, 232 E; 252/408

[56] References Cited

U.S. PATENT DOCUMENTS

| 934,500 | 9/1909 | Bouchaub-Praceig | 23/230 R |
|---|---|---|---|
| 3,410,663 | 11/1968 | Reilly et al. | 23/230 R |
| 3,997,297 | 12/1976 | Jenkins et al. | 23/232 E |

Primary Examiner—R.E. Serwin
Attorney, Agent, or Firm—R. S. Sciascia; Roy Miller; Lloyd E. K. Pohl

[57] ABSTRACT

A method for analyzing water for $\alpha$-trinitrotoluene comprising the steps of allowing the water to flow over an ion exchange resin which contains a quaternary ammonium group and observing to determine whether or not a chemical reaction takes place.

8 Claims, No Drawings

ANALYTICAL METHOD FOR TNT IN WATER

BACKGROUND OF THE INVENTION

1. Field of the Invention

This invention relates to (1) a method for analyzing water to determine whether or not it contains α-trinitrotoluene and (2) to a method for determining how much α-trinitrotoluene is present.

2. Description of the Prior Art

Trinitrotoluene (TNT), being a common explosive, is naturally handled in ammunition depots. Often, outmoded ordinance is washed out with water as a part of a handling process. This water gets added to other water used in the depot and thus forms part of the depot's effluent water.

The Environmental Protection Agency has formulated rules governing the amount of α-trinitrotoluene that may be present in effluent water and also requires that those who place water containing α-trinitrotoluene in streams or the like obtain a license. Accordingly, it is imperative that it be determined whether or not effluent water from an ammunition depot contains α-trinitrotolunene. Further, if effluent water does contain α-trinitrotoluene, it is desirable to have a method for quantitatively analyzing the water for the trinitrotoluene. In other words, the first question asked by the analyst is: Is α-TNT present? If the answer to this question is affirmative, the next question is; How much?

In the past, methods used in analyzing for TNT have involved evaporation steps (to concentrate the TNT) or extraction steps. These steps are time consuming. It would be advantageous if a method eliminating such steps were available. That is, it would be advantageous if a method whereby a large amount of effluent water could be analyzed without the necessity for concentrating the TNT or extracting it.

SUMMARY OF THE INVENTION

According to this invention, a sample of effluent water which may or may not contain α-TNT is flowed over either (1) a column of quaternary ammonium containing ion exchange resin that contains quaternary ammonium groups which has been coated with a fluorescent dye or (2) a thin film of such an ion exchange resin. If a dye coated column is used and if the water contains α-TNT, the fluorescence of the dye will decrease. A quantitative analysis of the α-TNT present may be obtained by measuring the amount of decrease in fluorescence. If a thin film of resin is used, what is surmised to be a chemical reaction between the α-TNT and the quaternary ammonium groups causes the film to darken. The darkening may be detected by placing a light on one side of the film and observing the film from the other side. The extent of the darkening provides a means whereby the quantity of α-TNT present may be estimated.

DESCRIPTION OF THE PREFERRED EMBODIMENT

Any ion exchange resin that darkens when reacted with α-TNT may be used in the practice of this invention. It has been found that resins which contain quaternary ammonium groups darken when reacted with α-TNT. Two specific examples of such resins are those sold under the tradenames of Dowex-2 and Permatit S-1. However, these two are by no means the only suitable resins. All that is necessary to render a resin suitable is that the resin darken when reacted with α-TNT. A resin would be suitable whether or not it contained quaternary ammonium groups if it darkened when reacted with α-TNT.

The sensitivity of quaternary ammonium containing resins for α-TNT is high and fairly specific. The main interfering compounds are isomeric TNT's and dinitrotoluenes, but this is actually useful since all are poisonous materials in water.

The best modes of practicing the invention involves coating a column of suitable resin with a flurorescent dye prior to carrying out the sensitivity of the resin to TNT or dinitrotoluene. If a α-TNT is present, the fluorescence of the dye decreases when it is contacted by the TNT.

As an alternative, a film of resin may be utilized. If a film is used, the need for a dye is eliminated.

Two dyes that have been found suitable thus far are rhodamine-B and sodium fluoroscein (uranine). As in the case of the aforementioned resins, these two dyes are merely examples and by no means exhaust the list. Any fluorescent dye which will stay on the resin when the resin is painted with it, dipped in it, sprayed with it or coated with it in any other manner is suitable.

If a resin film rather than a dye coated resin column is used, observation (as pointed out above) may be carried out by placing a light on one side of the film and observing the film from the other side to determine whether or not darkening takes place. It will be apparent to those skilled in the art that a color code can be readily made up by flowing samples of water containing known amounts of α-TNT over resin films and noting the amount of darkening that each amount causes. Thus, this technique provides not only a qualitative but a quantitative method.

Similarly, if a dye coated column is used, a quantitative standard may be readily developed by flowing samples of water containing known amounts of α-TNT over the columns and recording how much fluorescence decreases for each given amount of α-TNT.

It has been said above that one means for practicing the invention requires the use of a dye coated "column" of resin. It will be apparent to those skilled in the art that the "column" need not be a column as thought of in the ordinary sense of the word. That is, even if a dye is used the "column" may be a resin film that would be perfectly suitable for practicing the aforementioned alternative, i.e., the alternative where no dye is used.

Whichever means for practicing the invention is chosen the amount of water that is allowed to flow over the column or film should be the same as those amounts used in establishing the standard. Relatively large amounts of water may be tested. That is, there is no need for concentration or extraction steps. Also, when practicing the invention the columns or films used should be similar in geometrical shape and dimensions to those used in establishing the standard. Also, it should be pointed out that the quality control used in preparing the resin will determine the sensitivity of the system. Various optical methods can obviously be used to improve the performance and sensitivity.

It should be pointed out here that materials other than TNT could be analyzed for using similar techniques if it were found that such materials produced specific darkening reactions.

What is claimed is:

1. A method for determining whether or not trinitrotoluene is present in water comprising the steps of:

A. allowing a sample of said water to flow over an ion exchange resin that is coated with a fluorescent dye; and
B. observing whether or not the fluorescence of the dye changes.

2. A method according to claim 1 wherein said fluorescent dye is rhodamine-B.

3. A method according to claim 2 wherein said fluorescent dye is fluoroscein.

4. A method according to claim 1 wherein said ion exchange resin contains quaternary ammonium groups.

5. A method according to claim 4 wherein said fluorescent dye is rhodamine B.

6. A method according to claim 4 wherein said fluorescent dye is fluoroscein.

7. A method for determining whether or not trinitrotoluene is present in water comprising the steps of:
A. allowing a sample of said water to flow over a film of resin which changes color when reacted with trinitrotoluene; and
B. observing said resin to determine whether or not a color change takes place.

8. A method according to claim 7 whrerein said resin is a resin which contains quaternary ammonium groups.

* * * * *